US007695681B2

(12) United States Patent
Wang et al.

(10) Patent No.: US 7,695,681 B2
(45) Date of Patent: Apr. 13, 2010

(54) MINIATURE CHEMICAL ANALYSIS SYSTEM

(75) Inventors: Li-Peng Wang, San Jose, CA (US);
Qing Ma, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 1412 days.

(21) Appl. No.: 11/096,814

(22) Filed: Mar. 31, 2005

(65) Prior Publication Data
US 2006/0222568 A1    Oct. 5, 2006

(51) Int. Cl.
G01N 29/34    (2006.01)
G01N 29/14    (2006.01)

(52) U.S. Cl. .............................. 422/89; 422/70; 422/83; 422/88; 210/656; 95/827; 95/88; 95/89; 96/101; 73/23.4

(58) Field of Classification Search ................ 73/19.02, 73/23.35–23.42; 210/656; 422/70, 89, 83, 422/88; 95/82–89; 96/101–107
See application file for complete search history.

(56) References Cited

U.S. PATENT DOCUMENTS

| 4,735,906 | A  | 4/1988  | Bastiaans       |
| 4,789,804 | A  | 12/1988 | Karube et al.   |
| 5,501,986 | A  | 3/1996  | Ward et al.     |
| 5,552,274 | A  | 9/1996  | Oyama et al.    |
| 5,705,399 | A  | 1/1998  | Larue           |
| 5,763,283 | A  | 6/1998  | Cernosek et al. |
| 5,814,525 | A  | 9/1998  | Renschler et al.|
| 5,852,229 | A  | 12/1998 | Josse et al.    |
| 5,910,286 | A  | 6/1999  | Lipskier        |
| 5,932,953 | A  | 8/1999  | Drees et al.    |
| 6,096,656 | A  | 8/2000  | Matzke et al.   |
| 6,171,378 | B1 | 1/2001  | Manginell et al.|
| 6,289,286 | B1 | 9/2001  | Andersson et al.|
| 6,329,824 | B1 | 12/2001 | Tsuzuki et al.  |
| 6,348,795 | B2 | 2/2002  | Pringle, Jr. et al. |
| 6,630,309 | B2 | 10/2003 | Willner et al.  |
| 6,842,088 | B2 | 1/2005  | Yamada et al.   |
| 6,848,295 | B2 * | 2/2005 | Auner et al. ............... 73/24.06 |

(Continued)

FOREIGN PATENT DOCUMENTS

WO    WO-2004017063    2/2004

OTHER PUBLICATIONS

Lehmann et al. Sensor Proceedings, 2003, pp. 157-161.*

(Continued)

*Primary Examiner*—Jill Warden
*Assistant Examiner*—Shogo Sasaki
(74) *Attorney, Agent, or Firm*—Blakely, Sokoloff, Taylor & Zafman LLP

(57) ABSTRACT

An apparatus, according to one aspect, may include a chromatograph and a bulk acoustic resonator. The chromatograph may include a channel that is defined at least partially in a monolithic substrate. The channel may have an inlet to receive a sample and an outlet. A chromatography material may be included in the channel. The bulk acoustic resonator may have a first electrode and a second electrode that has a chemically functionalized surface. The chemically functionalized surface may be included in a chamber that is defined at least partially in the monolithic substrate and that is coupled with the outlet of the channel. Methods of making and using such apparatus, and systems including such apparatus, are also disclosed.

18 Claims, 9 Drawing Sheets

U.S. PATENT DOCUMENTS

| | | | |
|---|---|---|---|
| 6,906,919 | B2 | 6/2005 | Pokharna et al. |
| 2004/0019462 | A1* | 1/2004 | Gehrlein et al. ............. 702/188 |
| 2004/0056016 | A1* | 3/2004 | Tian et al. ................... 219/408 |
| 2004/0101990 | A1* | 5/2004 | Dunn et al. ................... 438/48 |
| 2004/0150296 | A1 | 8/2004 | Park et al. |
| 2004/0194628 | A1* | 10/2004 | Mitra ........................... 96/101 |
| 2005/0148065 | A1 | 7/2005 | Zhang et al. |
| 2006/0160144 | A1 | 7/2006 | Fendler |

OTHER PUBLICATIONS

Lehmann et al. Micro Total Analysis Systems, 2000, pp. 167-170.*

Lehmann et al. Sensor 99 Proceedings I, 1999, pp. 155-158.*

Lehmann et al. Sensor 2001 Proceedings II, 2001, pp. 487-492.*

Lehmann et al. Sensor 97, Kongerssband II, 1997, pp. 151-153.*

Agah, Masoud, et al., "Thermal Behavior of High-Performance Temperature-Programmed Microfabricated Gas Chromatography Columns", *Transducers '03, The 12th International Conference in Solid Sensors, Actuators and Microsystems*, Boston, MA, (Jun. 2003),pp. 1339-1342.

Kolesar Jr., Edward S., "Review and Summary of a Silicon Micromachined Gas Chromatography System", *IEEE Transactions on Components, Packaging, and Manufacturing Technology—Part B*, vol. 21, No. 4, (Nov. 1998),pp. 324-328.

Ruby, Richard C., et al., "Thin Film Bulk Wave Acoustic Resonators (FBAR) for Wireless Applications", *2001 IEEE Ultrasonics Symposium*, (2001),pp. 813-821.

Tian, Wei-Cheng, et al., "Microfabricated Preconcentrator—Focuser for a Microscale Gas Chromatograph", *Journal of Microelectromechanical Systems*, vol. 12, No. 3, (Jun. 2003),pp. 264-272.

Weigel, Robert, et al., "Microwave Acoustic Materials, Devices and Applications", *IEEE Transactions on Microwave Theory and Techniques*, vol. 50, No. 3, (Mar 2002),pp. 738-749.

Gabl, R., et al., "First results on label-free detection of DNA and protein molecules using a novel integrated sensor technology based on gravimetric detection principles", *Biosensors & Bioelectronics*, vol. 19, Issue 6, http://www.sciencedirect.com/science/journal/09565663,(Jan. 2004),pp. 615-620.

Gabl, R., et al., "Novel Integrated FBAR Sensors: A Universal Technology Platform for Bio- and Gas-Detection", *IEEE*, vol. 2 of 2, (Oct. 2003),pp. 1184-1188.

Zhang, Bo, et al., "A novel piezoelectric quartz mirco-array immunosensor based on self-assembled monolayer for determination of human chorionic gonadotropin", *Biosensors & Bioelectronics* vol. 19, No. 7, Elsevier,(2004),711-720.

* cited by examiner

MINIATURE CHEMICAL ANALYSIS SYSTEM

BACKGROUND

1. Field

Embodiments of the invention relate to miniature chemical analysis systems, methods of making or using the miniature chemical analysis systems, or systems including the miniature chemical analysis systems.

2. Background Information

Some miniature chemical analysis systems incorporate a chromatograph and a surface acoustic wave resonator (SAW), which are fabricated on different substrates instead of monolithically. The chromatograph may separate chemical species and the SAW may detect the chemical species. The surface of the SAW may be altered to preferentially attach certain chemical species. Attachment of the chemical species may change the frequency of the SAW, which may be used for chemical analysis.

However, a SAW may potentially have certain disadvantages, such as, for example, having relatively large insertion loss, and/or having a frequency that is relatively insensitive to changes in mass loading. This may potentially to reduce the sensitivity of the chemical analysis.

Additionally, different types of chemical species may potentially attach to the same altered surface of the SAW. This may potentially hinder chemical detection and/or identification.

Still further, fabricated the chromatograph and SAW on different substrates, instead of monolithically, may lead to relatively large volumes of gas in the paths coupling the substrates, which may potentially reduce sensitivity and adversely affect chemical analysis, and/or which may potentially increase the size of the chemical analysis system.

BRIEF DESCRIPTION OF THE SEVERAL VIEWS OF THE DRAWINGS

The invention may best be understood by referring to the following description and accompanying drawings that are used to illustrate embodiments of the invention. In the drawings.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

I. First Exemplary Chemical Analysis System

Figure 1:
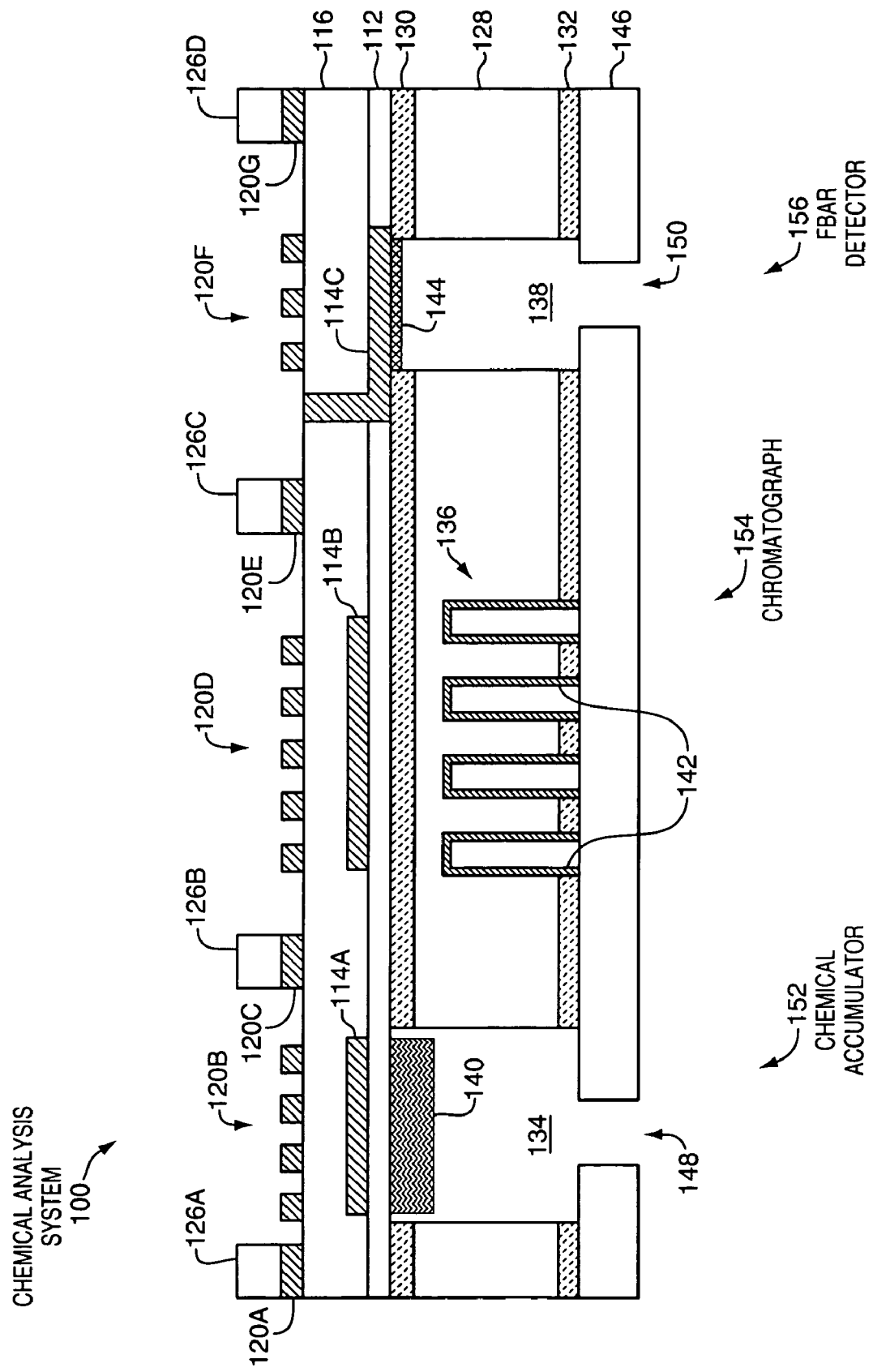
FIG. 1 shows a cross-sectional view of a miniature chemical analysis system formed monolithically on a silicon substrate, according to one or more embodiments of the invention.

FIG. 1 shows a cross-sectional view of an exemplary miniature chemical analysis system 100, according to one or more embodiments of the invention. The miniature chemical analysis system includes a sample inlet 148, an optional chemical accumulator 152, a chromatograph 154, a film bulk acoustic resonator (FBAR) detector 156, and a sample outlet 150. As shown, portions of each of the chemical accumulator, the chromatograph, and the FBAR detector may be defined at least partially in a monolithic substrate 128.

As used herein, the term "substrate" may refer to a workpiece object, such as, for example, a wafer or die, which may have portions that have been transformed by a sequence of operations or processes into miniature configurations, such as, for example, circuits and/or structures. A "monolithic" substrate may refer to a single piece of substrate, such as, for example, a single piece of silicon, semiconductor, or other substrate material. By way of example, the monolithic substrate may include a single die, wafer, or other piece of single crystal of silicon.

In order to further illustrate certain concepts, the chemical analysis system will be described in detail. The description will begin with the sample inlet, proceed through the chemical accumulator, chromatograph, and FBER detector, and finish with the sample outlet.

The chemical analysis system may receive a gas or other sample therein through the sample inlet 148. As shown, in one or more embodiments, the sample inlet may include a manifold or other opening in a coverplate 146. The coverplate may be bonded to or otherwise coupled with the monolithic substrate. In one or more embodiments of the invention, the sample inlet may be coupled with a sample source such as, for example, via tubing, valves, pumps, or the like. Alternatively, in one or more other embodiments, a membrane may be placed over the sample inlet and a syringe may be used to inject a sample therein.

The chemical accumulator 152 is coupled with the sample inlet and may receive the sample. As shown, in one or more embodiments of the invention, the chemical accumulator may be integral with the monolithic substrate. As used herein, the chemical accumulator is "integral" with the monolithic substrate when at least a portion of the chemical accumulator is formed from and/or in and/or on the monolithic substrate. As illustrated, a chamber 134 of the chemical accumulator may be housed or otherwise defined at least partially in the monolithic substrate.

The chemical accumulator includes a chemical accumulation material 140 within the chamber. Suitable chemical accumulation materials include, but are not limited to, sorbents and binding agents. Suitable sorbents include absorbents, adsorbents, and combinations thereof. The chemical accumulation material may sorb, bind, or otherwise accumulate one or more chemical species of interest from the sample selectively over one or more other chemical species, such as, for example, air or a carrier gas. Unsorbed chemical species may be removed, such as, for example, through the sample outlet 150, or through another outlet (not shown), which may optionally bypass the chromatograph.

The chemical accumulator may allow a chemical species to be accumulated and concentrated, such as, for example, from a gas that has the chemical species at low concentration and/or below a detection limit. The sorbed or otherwise accumulated chemical species may then be released at higher concentration and/or over the detection limit, as a sample plug with a narrow temporal width, which may help to reduce peak spreading within the chromatograph. The released chemical species may be removed from the chemical accumulator, such as, for example, a channel. Now, the chemical accumulator is optional and may be omitted, such as, for example, if the sample has the chemical species of interest above a detection limit or threshold.

The illustrated chemical analysis system includes a heater 120B. The heater is formed on a patterned aluminum nitride layer 116, which has sufficient thermal conductivity to transfer heat downward to the chemical accumulation material. The heater may be used to heat the chemical accumulation material in order to help release chemical species and to purge chemical species from the material, such as, for example, to increase sensitivity. As shown, in one or more embodiments, the heater may optionally include one or more resistive heating elements, such as, for example, one or more circuitous metal traces. The circuitous metal traces may be positioned over the chamber. Throughout the following description, it should be noted that terms such as "over", "under", "top", "bottom", "upper", "lower", "vertical", "horizontal", and the like, are used herein to facilitate the description of the system "as illustrated". It will be evident that the systems may be used in a variety of orientations including, but not limited to, inverted, and vertical orientations.

The illustrated system also includes an optional heat spreader 114A that is physically and thermally disposed between the heater and the chemical accumulation material. In one or more embodiments, the heat spreader may include a metal plate over the chamber of the chemical accumulator. Suitable metals for the heat spreader include, but are not limited to, molybdenum, gold, platinum, copper, aluminum, titanium, chromium, palladium, tungsten, and combinations thereof. These metals are also suitable for the heater. The heat spreader may receive heat from the heater and may spread or distribute heat to the chemical accumulation material. Such spreading or distribution of the heat may promote relatively more uniform heating of the material, and may allow more time-resolved release of chemical species. However, the heat spreader is not required.

The illustrated heat spreader is formed over, and directly on, a patterned silicon nitride layer 112. As shown, the silicon nitride layer may separate the heat spreader from the chemical accumulation material. Silicon nitride has sufficient thermal conductivity to transfer heat to the chemical accumulation material, may provide mechanical strength and reliability to the chemical analysis system, and is also somewhat electrically insulating. However, the use of silicon nitride is not required. Other materials besides silicon nitride may also optionally be used including, but are not limited to, oxynitrides.

The chemical analysis system includes several other layers that should be mentioned. The silicon nitride layer 112 is formed over, and directly on, a patterned upper silicon dioxide layer 130. The patterned upper silicon dioxide layer overlies, and is superjacent to, the monolithic substrate 128. A patterned lower silicon dioxide layer 132, underlies, and is subjacent to, the monolithic substrate. The patterned lower silicon dioxide layer overlies, is superjacent to, and may be bonded or otherwise attached to, the coverplate 146. As will be discussed further below, the silicon dioxide layers may be used as etch stop layers, although other layers may also optionally be used.

Referring again to FIG. 1, the chemical analysis system also includes the chromatograph 154. The chromatograph may be coupled with an outlet of the chemical accumulator and may receive the released chemical species. In one or more embodiments of the invention, the released chemical species may at least potentially include a mixture of two or more different chemical species. The chromatograph may separate the chemical species of the mixture.

As shown, in one or more embodiments of the invention, the chromatograph may be integral with the monolithic substrate. At least a portion of the chromatograph may be formed from and/or in and/or on the monolithic substrate. As illustrated, the chromatograph may include a channel 136 that may be housed or otherwise defined at least partially in the monolithic substrate.

The channel may have an inlet (not shown), such as, for example, at the left-handed side, and an outlet (not shown), such as, for example, at the right-hand side. The inlet of the chromatograph may be coupled with the outlet of the chemical accumulator, such as, for example, through a channel, to receive chemical species. The channel may have a length that is sufficient to temporally separate chemical species of a mixture. Depending, at least in part, upon the chemical species, the length of the channel may be elongated and may range from about 0.1 to 10 meters, for example. In order to help accommodate such lengths in small areas, the channel may have a winding, serpentine, interlocked spiral, or similar shape.

A chromatography material 142, which is also sometimes known in the art as a stationary-phase material, may be included in the channel. A wide variety of well-known chromatography materials are suitable. As shown, the chromatography material may optionally coat at least a portion of the walls and/or the ceiling of the channel. However, it is not required that the chromatography material be included in these locations, or in just these locations.

The chromatography material may affect the progression and/or the velocity of the chemical species through the channel based at least in part on their chemical properties. Each of the chemical species may have a different affinity and interaction with the chromatography material, and may correspondingly be delayed in the channel for a different period of time. This may allow the chemical species to be temporally separated. The temporally separated chemical species may be eluted or otherwise removed sequentially from the outlet of the chromatograph as a series of time-resolved peaks.

The illustrated system further includes an optional heater 120D over the chromatograph, and an optional heat spreader 114B disposed between the heater and the chromatograph. The heater and heat spreader may optionally have some or all of the characteristics of the corresponding heater and heat spreader described above. The chromatography material may optionally be heated during a separation, such as, for example, to improve or otherwise alter the separation, and/or optionally after a separation, such as, for example, to purge chemical species from the chromatography material, such as, for example, to help reduce contamination.

With continued reference to FIG. 1, the chemical analysis system further includes the FBAR detector 156. The FBAR detector may be coupled with the outlet of the chromatograph and may receive the temporally separated chemical species from the chromatograph.

As shown, in one or more embodiments of the invention, the FBAR detector may be integral with the monolithic substrate. At least a portion of the FBAR detector may be formed from and/or in and/or on the monolithic substrate. As illustrated, a chamber 138 of the FBAR detector may be housed or otherwise defined at least partially in the monolithic substrate. The chamber of the FBAR detector is defined in part by a patterned layer 112, which provides a structural membrane, and which is also formed monolithic over the silicon substrate.

Forming or otherwise providing the FBAR detector integral with the chemical accumulator and/or chromatograph may offer certain potential advantages. For one thing, this may allow a smaller or more miniaturized chemical analysis system. For another thing, this may help to improve chemical sensitivity and analysis. Often the FBAR detector may be coupled with the chromatograph via a microchannel defining a small volume of gas. The amount of gas may be substantially less than would be present in a path coupling an off-substrate resonator with the chromatograph if they were not monolithically integrated.

The FBAR detector also includes a first, upper electrode 120F, and a second, lower electrode 114C having a coated or otherwise chemically functionalized surface. The electrodes may each include a metal or other conductive material.

As shown, in one or more embodiments of the invention, rather than a planar electrode, the upper electrode 120F may optionally include one or more circuitous metal or otherwise conductive traces over the lower planar electrode. The circuitous metal traces may optionally be used as resistive heating elements to heat the lower electrode, such as, for example, to help control the temperature of the FBAR detector. As further shown, in one or more embodiments, the lower electrode of the FBAR detector may optionally be formed in an opening in a silicon nitride layer 112. Although not required, this may potentially help to reduce acoustic energy loss from the FBAR detector.

In one or more embodiments, the heater 120B of the chemical accumulator, the heater 120D of the chromatograph, and the upper electrode 120F of the FBAR detector may optionally be formed from a single first patterned metal layer. Likewise, the heat spreader 114A of the chemical accumulator, the heat spreader 114B of the chromatograph, and the lower electrode 114C of the FBAR detector may optionally be formed from a single second patterned metal layer. In one or more embodiments of the invention, in order to provide an FBAR detector with relatively low acoustic energy loss, either or both of the first and second patterned metal layers may include a metal that provides a substantially low acoustic energy loss, such as, for example, molybdenum or tungsten. This may help to provide an FBAR detector with a relatively high Q-value. However, the scope of the invention is not limited in this respect. Additionally, there is no requirement that the electrodes and the heaters and/or heat spreaders be formed from single layers or include the same metal.

Disposed immediately between the upper and lower electrodes is a portion of the patterned aluminum nitride layer 116. The aluminum nitride layer also overlies, and is superjacent to, both the silicon nitride layer 112 and the heat spreaders 114A, 114B. The aluminum nitride layer also underlies, and is subjacent to, the heaters 120B, 120D.

Aluminum nitride (AlN) is a piezoelectric material. During operation, when a signal is applied to the electrodes, the FBAR detector may resonate at a particular frequency. As is known, the resonance frequency may depend upon the thickness of the material between the electrodes and on the properties of the material, such as, for example, acoustic velocity. For aluminum nitride, a sufficient thickness may range from about 1 to 3 μm, although the scope of the invention is not limited to just these thickness. Other suitable piezoelectric materials besides aluminum nitride include, but are not limited to, zinc oxide (ZnO), piezoceramic, such as, for example, lead-zirconate titanate (PZT), and quartz.

Now, the FBAR detector may be used to sense, detect, identify, or otherwise chemically analyze at least one or all of the chemical species received into the chamber. The lower electrode has the chemically functionalized surface 144. In various embodiments of the invention, the chemically functionalized surface may include a material, coating, layer, monolayer, or surface treatment that is applied to, formed over, or otherwise included over the lower electrode. Different approaches for forming the chemically functionalized surface are described further below.

The chemically functionalized surface is included in the chamber of the FBAR detector and is accessible to chemical species therein. The chemical species may potentially react, bind, sorb, or otherwise attach to or couple with the chemically functionalized surface. Such attachment may change the resonance frequency of the FBAR detector due, at least in part, to a change in mass loading. Typically, the attachment will result in a decrease in the resonance frequency. The change in the resonance frequency may be determined and used to analyze the chemical species, such as, for example, to quantitatively detect the chemical species. In one or more embodiments of the invention, the chemically functionalized surface may specifically attach one molecule or a small subset of molecules and the change may allow chemical identification. Additional information, such as, for example, time to elute from the chromatograph may also optionally be used to facilitate chemical identification.

FBAR detectors may offer certain potential advantages over other resonators that have been used for chemical analysis. For one thing, FBAR detectors may tend to have relatively smaller insertion loss, such as, for example, substantially less than 35 dB. Further, the resonance frequencies of FBAR detectors may tend to be relatively more sensitive to changes in mass loading. Other bulk acoustic resonators may offer similar advantages and are suitable for embodiments of the invention.

Referring again to FIG. 1, an outlet of the chamber of the FBAR detector may be coupled with the sample outlet 150 to allow chemical species to be removed from the chemical analysis system. As shown, in one or more embodiments, the sample outlet may include a manifold or other opening in the coverplate. In one aspect, the manifold or opening may allow the chemical analysis system to be coupled with an external sample destination where the sample or a portion thereof may be disposed. External coupling devices, such as, for example, tubing, valves, pumps, and like devices, and combinations thereof, may be used for the coupling.

With continued reference to FIG. 1, the chemical analysis system further includes optional seed materials 120A, 120C, 120E, and 120G. In one or more embodiments of the invention, the seed materials may be part of the same patterned metal layer as the heaters and upper electrode. Over, and directly on, the seed materials are bonding pads 126A, 126B, 126C, and 126D. In one or more embodiments of the invention, the bonding pads may optionally be plated or otherwise formed over, or directly on, the seed materials. The bonding pads and seed materials together represent signaling paths or signaling mediums that may be used to communicate signals to and/or from the chemical analysis system. The signals may be used to provide control and/or other information to the chemical analysis system from external circuits and/or to deliver chemical analysis results and/or other information from the chemical analysis system to external circuits.

II. Method of Forming First Chemical Analysis System

FIGS. 2-7 show cross-sectional views of substrates representing different stages of a method of fabricating a chemical analysis system similar to that shown in FIG. 1, according to one or more embodiments of the invention. In these figures, certain reference numerals have been repeated to indicate that components may correspond.

Figure 2:
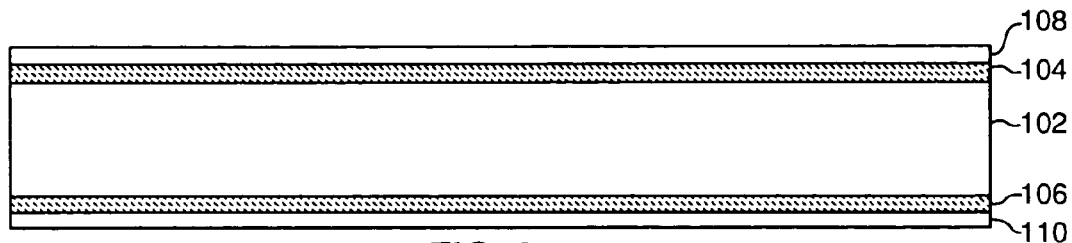
FIGS. 2-7 show cross-sectional views of substrates representing different stages of a method of fabricating a miniature chemical analysis system similar to that shown in FIG. 1, according to one or more embodiments of the invention.

FIG. 2 shows a view of a monolithic silicon substrate 102, an upper silicon dioxide layer 104, a lower silicon dioxide layer 106, an upper silicon nitride layer 108, and a lower silicon nitride layer 110, according to one or more embodiments of the invention. The silicon dioxide layers may be formed on the monolithic silicon substrate by deposition or thermal growth. A sufficient thickness may be, for example, between about 0.3 to 2 μm. The silicon nitride layers may be deposited on the silicon dioxide layers, such as, for example, by using low-pressure chemical vapor deposition (LPCVD). A sufficient thickness may be, for example, between about 0.5 to 4 μm.

Figure 3:
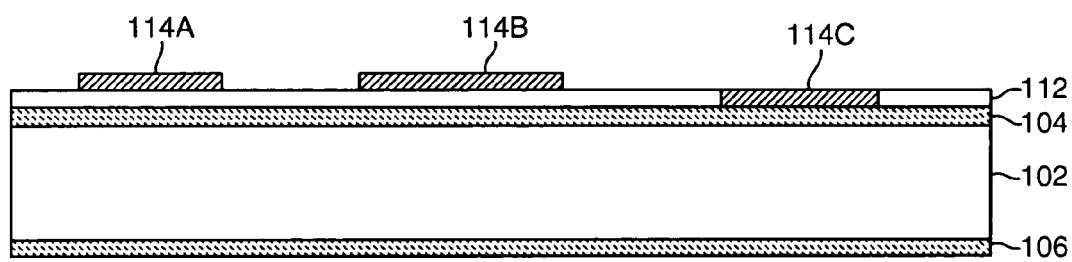

FIG. 3 shows a view after selectively etching the silicon nitride layers of the substrate of FIG. 2, and then forming a patterned metal layer over the upper surface of the resulting substrate, according to one or more embodiments of the invention. During the silicon nitride etch, the lower silicon nitride layer may be entirely removed using the lower silicon dioxide layer as an etch stop. An opening may also be etched in the upper silicon nitride layer in a region that is to contain the lower electrode 114C of the FBAR detector. A patterned resist layer or other patterned mask may be used to perform the patterned etch of the upper silicon nitride layer also using the upper silicon dioxide layer as an etch stop.

Then, after etching the upper silicon nitride layer, a patterned metal layer may be formed over the upper surface of the resulting substrate. Initially, a metal layer may be deposited over the upper surface, such as, for example, by evaporation or sputtering. Then, the metal layer may be patterned, such as, for example, by photolithography and lift-off or etching. As shown, the resulting patterned metal layer may include a first metal portion 114A corresponding to the heat spreader of the chemical accumulator, a second metal portion 114B corresponding to the heat spreader of the chromatograph, and a third metal portion 114C corresponding to the lower electrode of the FBAR detector.

Figure 4:
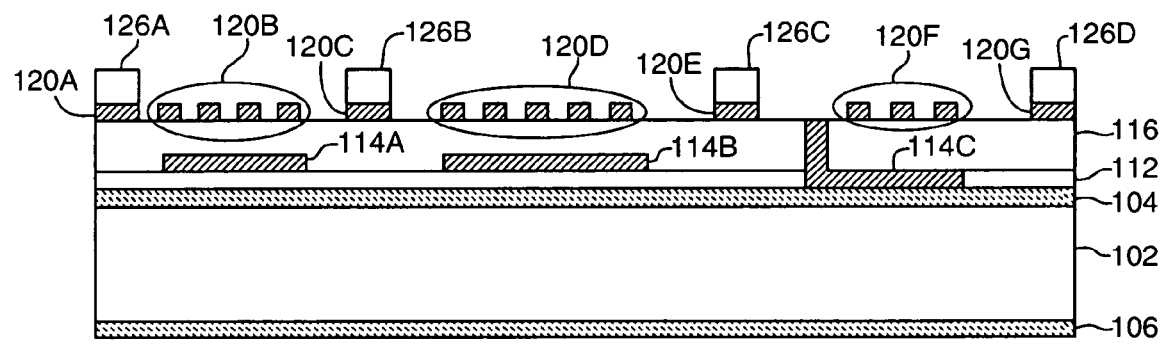

FIG. 4 shows a view after forming a patterned aluminum nitride layer 116 over the substrate of FIG. 3, forming a patterned metal layer 120A-G over the aluminum nitride layer, and plating or otherwise forming bonding pads 126A-D over corresponding seed material portions 120A, 120C, 120E, and 120G of the patterned metal layer, according to one or more embodiments of the invention. First, the aluminum nitride layer may be deposited, such as, for example, by reactive sputtering. A sufficient thickness may range from about 0.5 to 3 μm, for example. Then, an opening may be formed through the aluminum nitride layer proximate the lower electrode 114C of the FBAR detector, such as, for example, by performing a patterned etch according to a patterned mask.

Then, the patterned metal layer may be formed over the aluminum nitride layer either before, but typically after, the patterning of the aluminum nitride layer. The patterned metal layer may include seeds materials 120A, 120C, 120E, and 120G. The patterned metal layer may also include circuitous metal traces 120B, 120D, and 120F, which correspond to the chemical accumulator, chromatograph, and FBAR detector, respectively. The patterned metal layer may also include metal in the opening in the aluminum nitride layer to provide a signal path or medium to the lower electrode. In one or more embodiments of the invention, the thickness of a patterned metal layer may range from about 0.1 to 0.4 μm, although the scope of the invention is not limited in this respect. The width of the metal traces may vary depending upon the implementation and may optionally be different for the chemical accumulator, the chromatograph, and/or the FBAR detector. The bonding pads may then be formed over the seed materials, such as, for example, by plating.

Figure 5:
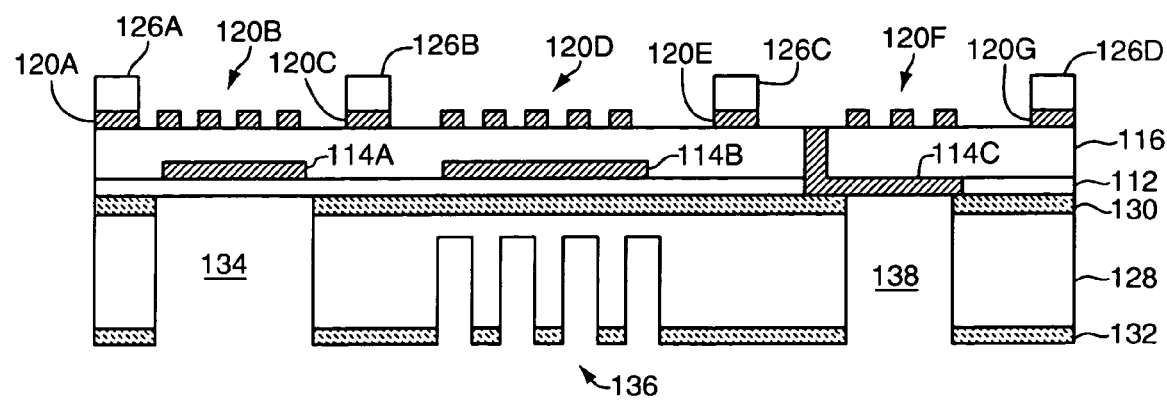

FIG. 5 shows a view after forming openings in the backside of the substrate of FIG. 4, according to one or more embodiments of the invention. The openings include a first opening 134 corresponding to the chamber of the chemical accumulator, a second opening 136 corresponding to the channel or column of the chromatograph, and a third opening 138 corresponding to the chamber of the FBAR detector. The openings are each formed at least in part by removing material of the monolithic substrate. In one or more embodiments of the invention, a patterned resist layer or other patterned mask may be formed over a lower surface of the substrate, such as, for example, over the lower silicon dioxide layer 132, and then an etch may be performed to form the openings according to the patterned resist layer. In one or more embodiments, a deep reactive ion etch (DRIE) may optionally be used to obtain different etch rates, such as, for example, as a function of the aspect ratio of the openings, although this is not required. As shown, this may optionally allow deeper openings to be formed for the chambers than for the channel.

Figure 6:
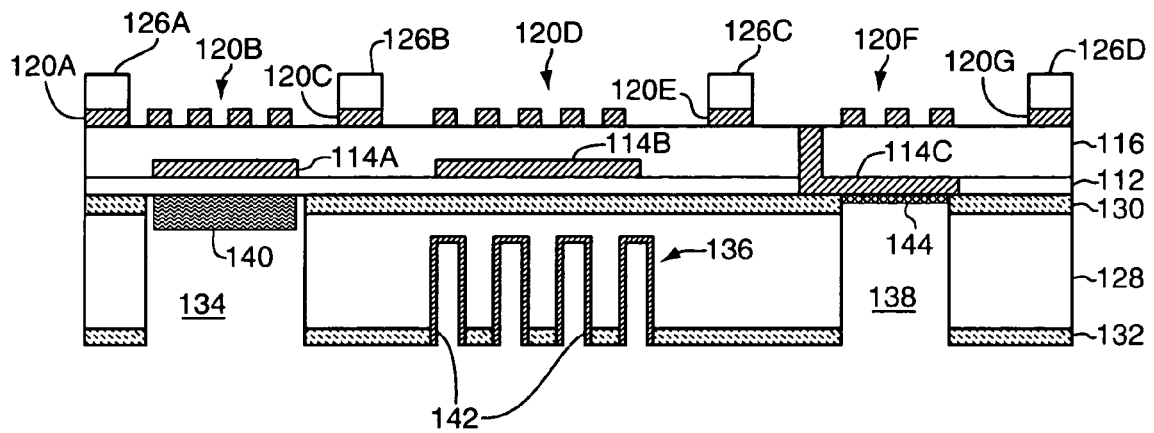

FIG. 6 shows a view after introducing materials into the openings of the substrate of FIG. 5, according to one or more embodiments of the invention. A chemical accumulation material 140 has been introduced into the chamber of the chemical accumulator. A chromatography material 142 has been introduced into the channel of the chromatograph. A material has been introduced to provide a chemically functionalized surface 144 on the lower electrode of the FBAR detector. Note that it is not required that the materials be introduced in the positions illustrated, or only in the positions illustrated.

Depending at least in part on the particular material, suitable approaches for introducing materials include, but are not limited to, localized syringe, nanodispensing, spin coating, dip coating, localized spray coating, and combinations of such approaches. In one or more embodiments, the materials are introduced sequentially, in order to help avoid thermal damage to a previously introduced material. Materials that are relatively more thermally stable, and/or that are applied at a higher temperature, may optionally be applied before materials that are less thermally stable, and/or that are applied at a lower temperature. In some instances, drying may optionally be used to remove liquid from the materials.

Various approaches may be used to chemically functionalize the electrode surface. In general, the surface may be chemically functionalized by introducing one or more different types of molecules, biomolecules, or other materials thereto.

One approach may include self-assembling molecular or biomolecular layers on the surface. Suitable biomolecules include, but are not limited to, amino acid derivatized fatty acids, amino acid derivatized lipids, and other molecules.

Another approach may include forming a self-assembled monolayer on the surface and then immobilizing molecules or biomolecules on the self-assembled monolayer. Examples of suitable molecules include, but are not limited to, a variety of polymeric molecules. Examples of suitable biomolecules include, but are not limited to, antibodies and DNA molecules. Other suitable biomolecules include fragments and derivatives of such biomolecules. As one example, a self-assembled monolayer of a thiol, sulfide, or like species may be formed on the electrode surface, such as, for example, by chemisorption, and then antibodies, DNA molecules, or other biomolecules may be covalently linked to the self-assembled monolayer using an activation process. The antibodies or DNA molecules may provide a relatively specific chemically functionalized surface that may target a specific molecule or a substantially small group of molecules.

Yet another approach may include forming an organic membrane on the surface. The organic membrane may be formed by pre-coating, chemical derivatization, or photo-bonding, to name just a few examples. Examples of chemical derivatization include, but are not limited to, silylation, acylation, esterification or alkylation.

A further approach may include forming an organic membrane on the surface, and then immobilizing molecules or biomolecules on the organic membrane. A still further approach may include direct immobilization of molecules or biomolecules on metal. Another approach may include direct immobilization of biomolecules on a non-metallic inorganic film. Still other approaches include, but are not limited to, coating or applying organic, polymeric, halogenated polymeric, organometallic, inorganic, silicone, and metal materials over the surface of the electrode. Still further approaches known in the art for functionalizing surfaces of SAWs may also optionally be used.

Figure 7:
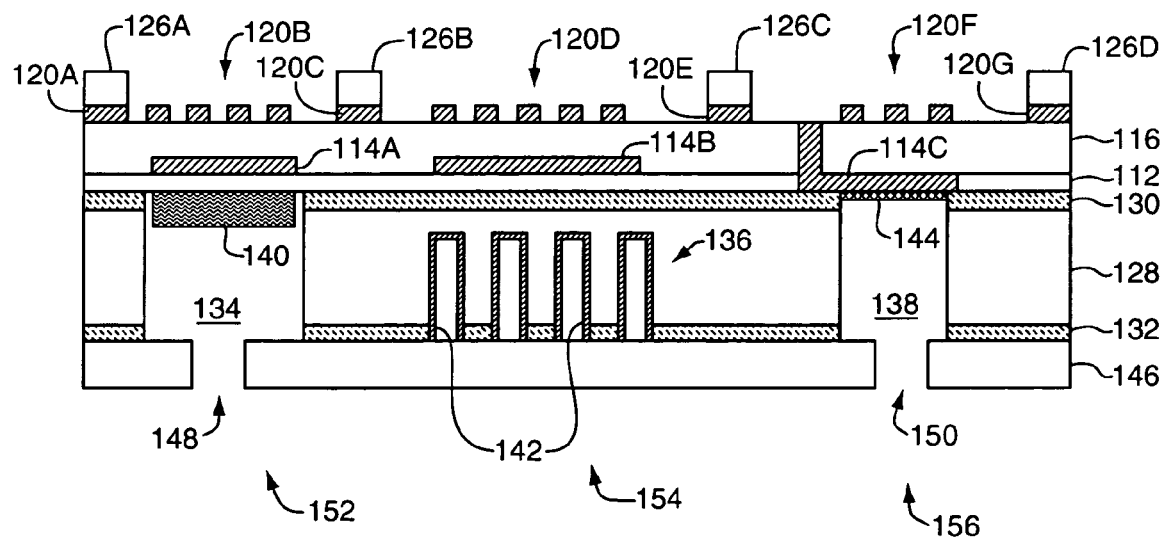

FIG. 7 shows a view after attaching a coverplate 146 having a sample inlet manifold or opening 148 and a sample outlet manifold or opening 150 therein to the backside of the substrate of FIG. 6, according to one or more embodiments of the invention. In one or more embodiments of the invention, the coverplate may include a glass substrate that may be attached with anodic bonding, although this is not required. Other suitable substrates include, but are not limited to, quartz substrates, organic substrates, and metal substrates, which may be attached with adhesives or otherwise.

III. Second Exemplary Chemical Analysis System

Figure 8:
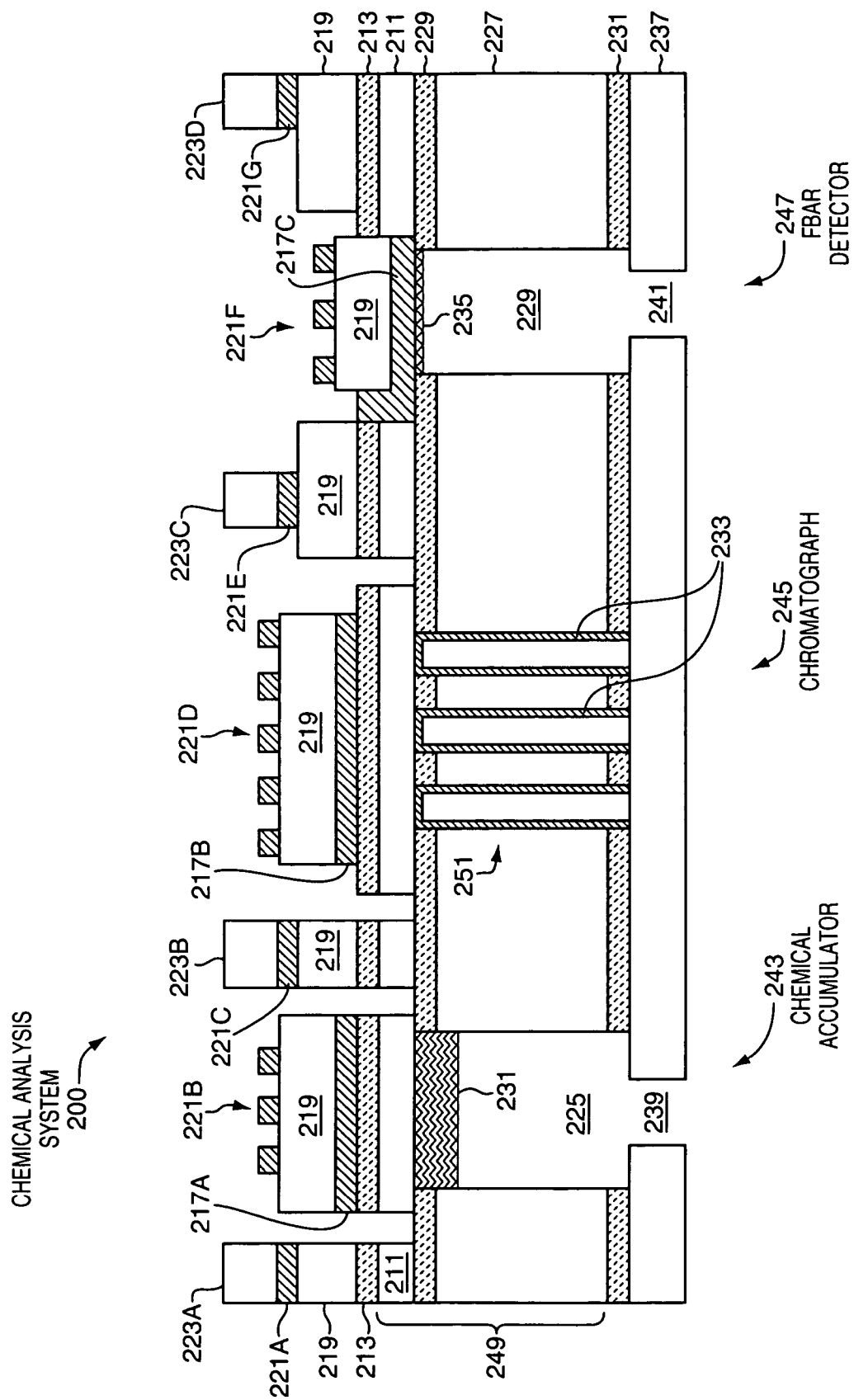
FIG. 8 shows a cross-sectional view of a miniature chemical analysis system formed monolithically on a silicon-on-insulator (SOI) substrate, according to one or more embodiments of the invention.

FIG. 8 shows a cross-sectional view of an exemplary miniature chemical analysis system 200 having an optional chemical accumulator 243, a chromatograph 245, and an FBAR detector 247 that are each integral with a patterned silicon-on-insulator (SOI) substrate 249, according to one or more embodiments of the invention. Many of the components of the chemical analysis system 200 may optionally have some or all of the characteristics of the correspondingly named components of the chemical analysis system 100 shown in FIG. 1. To avoid obscuring the following description, the different and/or additional characteristics and structures of the chemical analysis system 200 will be emphasized.

The illustrated chemical analysis system includes a coverplate 237 having a sample inlet 239 and sample outlet 241. As shown, the coverplate may be coupled with a backside of the patterned SOI substrate through an intervening patterned lower silicon dioxide layer 231.

The patterned SOI substrate includes patterned active silicon 211, patterned buried insulator 229, and patterned bulk silicon 227. As shown, the patterned SOI substrate has been transformed during fabrication of the chemical analysis system. The chemical analysis system is formed monolithically integral with the SOI substrate. As shown, portions of each of the chemical accumulator, chromatograph, and FBAR detector are integral with the patterned SOI substrate.

The chemical accumulator includes a chamber 225 that is housed or defined at least partially within the patterned SOI substrate. A sorbent or other chemical accumulation material 231 is included in the chamber. An optional heater 221B, such as, for example, including one or more circuitous metal traces, is positioned over the chamber to heat the chemical accumulation material. An optional heat spreader 217A is disposed between the heater and the chamber to spread or otherwise distribute heat.

The chromatograph includes a channel or column 251 that is housed or defined at least partially within the patterned SOI substrate. A chromatography material 233 is included in the channel. An optional heater 221D, such as, for example, including one or more circuitous metal traces, is positioned over the channel to heat the chromatography material. An optional heat spreader 217B is disposed between the heater and the channel to spread or otherwise distribute heat.

The FBAR detector includes a chamber 229, which is housed or defined at least partially within the patterned SOI substrate, a lower electrode 217C, and an upper electrode 221F. As viewed, the lower electrode forms a ceiling for the chamber and has a chemically functionalized surface 235. In one or more embodiments of the invention, the upper electrode may optionally include one or more circuitous metal traces that may be used to heat the lower electrode, such as, for example, to control its temperature and/or release attached chemical species.

In the illustrated embodiment, a patterned upper silicon dioxide layer 213 is included over, and directly on, the patterned active silicon 211. The upper silicon dioxide layer may be used as an etch stop, although other etch stops may also be used. The patterned upper silicon dioxide layer is disposed immediately between the heat spreaders and the underlying patterned active silicon. An opening is included through both the patterned upper oxide layer and the patterned active silicon to accommodate the lower electrode of the FBAR detector. Removing the oxide and active silicon in this region may help to reduce acoustic energy loss and may help to provide a resonator with a relatively higher Q-value, although this is not required.

The chemical analysis system also includes a patterned aluminum nitride layer 219. The patterned aluminum nitride layer is included over, and directly on, a portion of the patterned upper oxide layer 213, and over, and directly on, the heat spreaders 217A, 217B and lower electrode 217C, which may be part of the same patterned metal layer. The illustrated patterned aluminum nitride layer is disposed immediately between the heaters and the heat spreaders of the chemical accumulator and chromatograph. Additionally, the illustrated patterned aluminum nitride layer separates the upper and lower electrodes of the FBAR detector. As discussed above, other piezoelectric materials besides aluminum nitride may also optionally be used.

As shown, in one or more embodiments of the invention, vertical trenches or other openings may optionally be included around peripheries of the heaters and heat spreaders.

As shown, the trenches may optionally be formed down through the active silicon, although this is not required. The trenches may help to favor heat transfer from the heater to the materials included in the chambers and/or channel and may help to reduce conduction of heat in the horizontal direction or otherwise away from the materials in the chamber and/or channel.

Seed materials 221A, 221C, 221E, and 221G may be included over, and directly on, the patterned aluminum nitride layer. In one or more embodiments of the invention, the seed materials may be part of the same patterned metal layer as the heaters of the chemical accumulator and chromatograph and upper electrode of the FBAR detector. Bonding pads 223A, 223B, 223C, and 223D may be plated or otherwise formed over, or directly on, the corresponding underlying or subjacent seed materials.

Compared to a standard silicon substrate, the SOI substrate may tend to provide a mechanically stronger and potentially more reliable chemical analysis system. The patterned active silicon layer may tend to exhibit good mechanical strength. However, the SOI substrate may tend to be more costly than a standard silicon substrate.

IV. Method of Forming Second Exemplary Chemical Analysis System

FIGS. 9-15 show cross-sectional views of substrates representing different stages of a method of fabricating a chemical analysis system similar to that shown in FIG. 8, according to one or more embodiments of the invention. In these figures, certain reference numerals have been repeated to indicate that components may correspond. Certain operations, such as, for example, forming layers, patterning layers, and the like, may be similar to operations that have already been described above. For brevity, the following description may tend to emphasize different and/or additional details.

Figure 9:
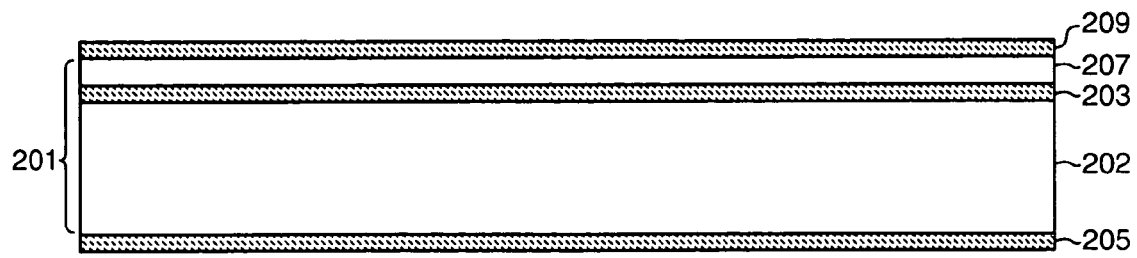
FIGS. 9-15 show cross-sectional views of substrates representing different stages of a method of fabricating a miniature chemical analysis system similar to that shown in FIG. 8, according to one or more embodiments of the invention.

FIG. 9 shows a view of an SOI substrate 201 having an upper silicon dioxide layer 209 and a lower silicon dioxide layer 205 formed thereon, according to one or more embodiments of the invention. The SOI substrate includes an active silicon layer 207, a buried silicon dioxide layer 203, and a bulk silicon layer 202. The upper and lower silicon dioxide layers may be formed on the SOI substrate by thermal growth or deposition.

Figure 10:
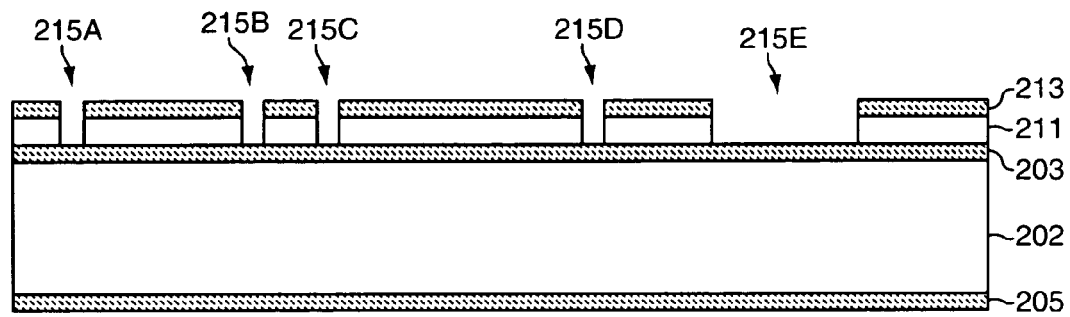

FIG. 10 shows a view after optionally etching or otherwise forming openings 215A-E in the upper surface of the substrate of FIG. 9, according to one or more embodiments of the invention. A first trench 215A, 215B may optionally be formed through the upper silicon dioxide layer and the active silicon layer around a periphery over the intended location of the chamber of the chemical accumulator. A second trench 215C, 215D may optionally be formed through the upper silicon dioxide layer and the active silicon layer around a periphery over the intended location of the channel of the chromatograph. As discussed above, these trenches, which are optional, may help to provide thermal insulation. An opening 215E may optionally be formed through the upper silicon dioxide layer and the active silicon layer in a region intended for the lower electrode of the FBAR detector. This opening may help to reduce acoustic energy loss and improve the Q-value of the FBAR detector, although it is not required.

Figure 11:
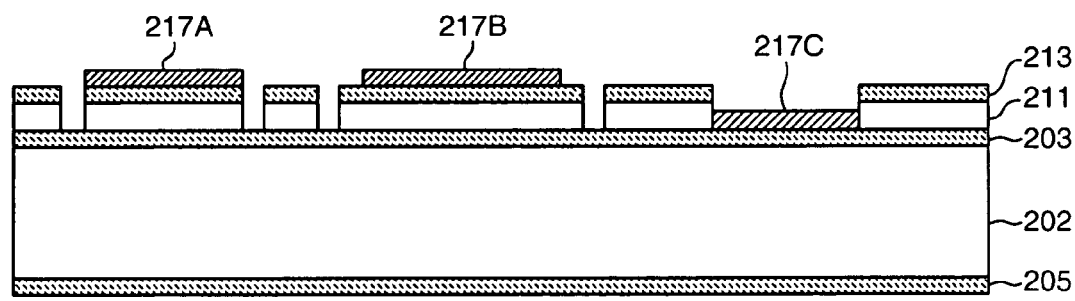

FIG. 11 shows a view after forming a patterned metal layer 217A-C over, and directly on, the upper surface of the substrate of FIG. 10, according to one or more embodiments of the invention. The patterned metal layer includes a first heat spreader 217A over the intended location of the chamber of the chemical accumulator, a second heat spreader 217B over the intended location of the channel of the chromatograph, and a lower electrode 217C over the intended location of the chamber of the FBAR detector.

Figure 12:
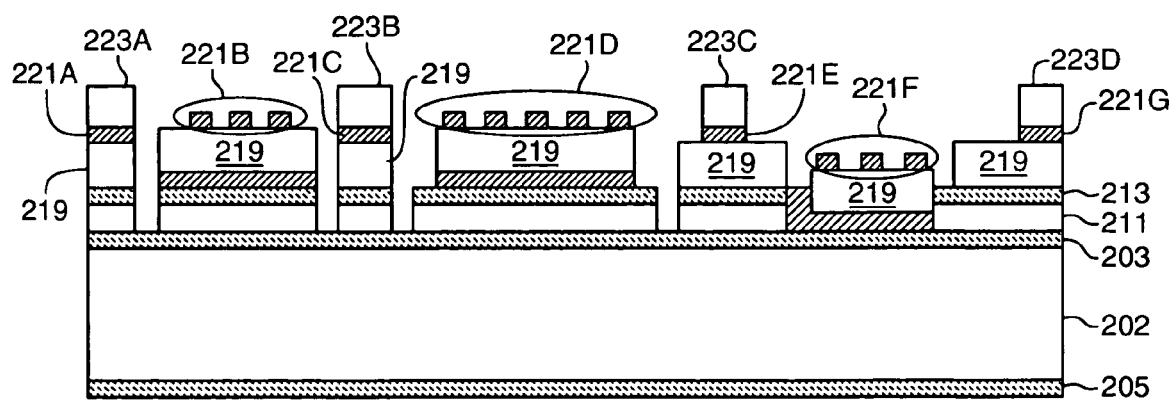

FIG. 12 shows a view after forming a patterned aluminum nitride layer 219 over the substrate of FIG. 11, forming a patterned metal layer 221A-G over the aluminum nitride layer, and plating or otherwise forming bonding pads 223A-D over seed materials 221A, 221C, 221E, and 221G of the patterned metal layer, according to one or more embodiments of the invention. In one or more embodiments, the aluminum nitride layer may be patterned by using the patterned oxide layer 213 as an etch stop, although this is not required. As shown, in one or more embodiments, trenches or other openings may optionally be formed through the aluminum nitride layer over the existing trenches or openings. An opening may optionally be formed over the FBAR detector.

Figure 13:
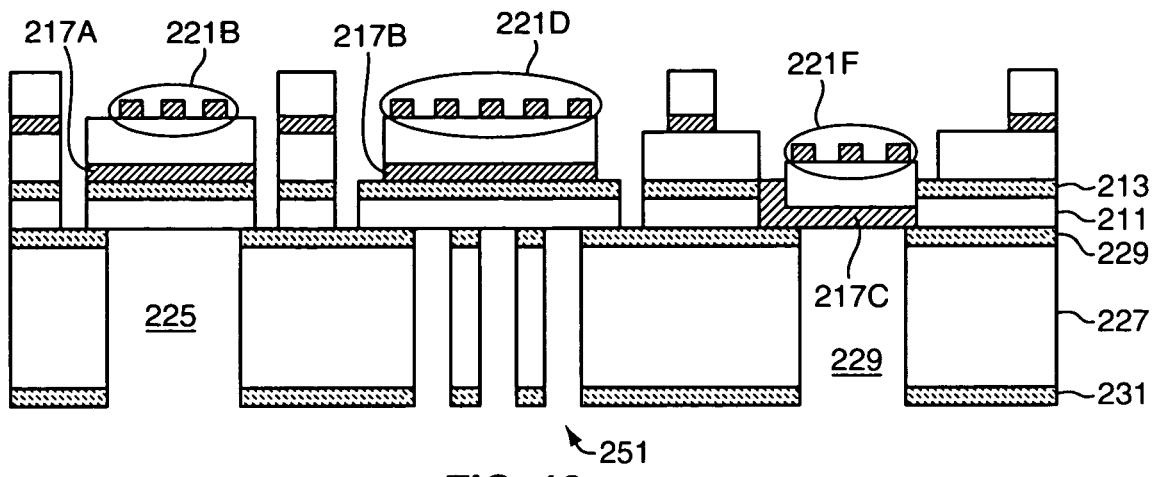

FIG. 13 shows a view after etching or otherwise forming chamber 225, 229 and channel 251 openings in the backside of the substrate of FIG. 12, according to one or more embodiments of the invention. The illustrated openings are formed through the lower silicon dioxide layer, the bulk silicon layer, and the buried silicon dioxide layer, although this is not required. In one or more embodiments of the invention, the openings may be formed by first performing a silicon etch according to a patterned mask in order to etch through the lower silicon dioxide layer and the bulk silicon layer, and then a silicon dioxide etch may be performed with the self-aligned bulk silicon as a mask to etch through the buried silicon dioxide layer. The etching through the silicon dioxide layer may expose the lower electrode of the FBAR detector.

Figure 14:
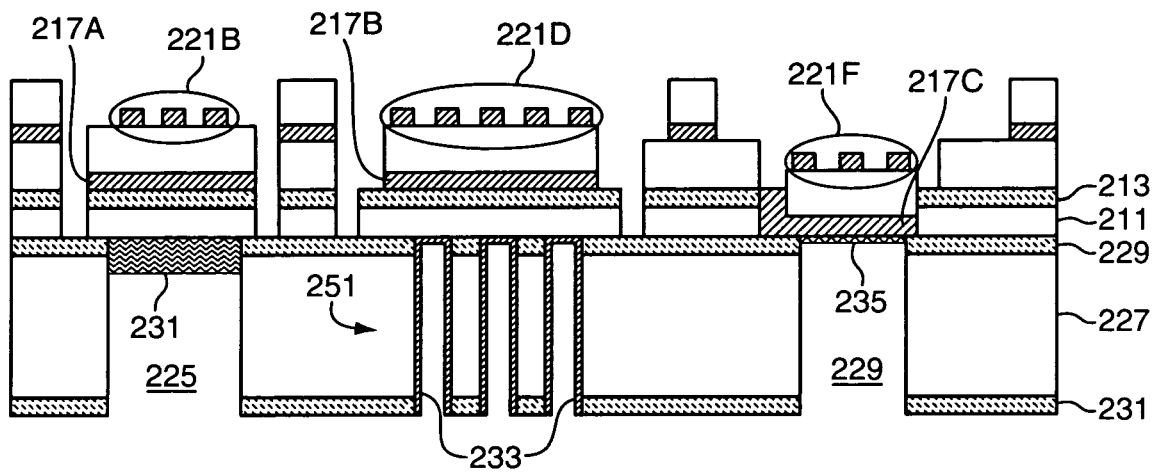

FIG. 14 shows a view after introducing a chemical accumulation material 231 into the chamber 225 of the chemical accumulator, introducing a chromatography material 233 into the channel 251 of the chromatograph, and chemically functionalizing a surface 235 of the lower electrode of the FBAR detector, according to one or more embodiments of the invention. The approaches described above may optionally be used.

Figure 15:
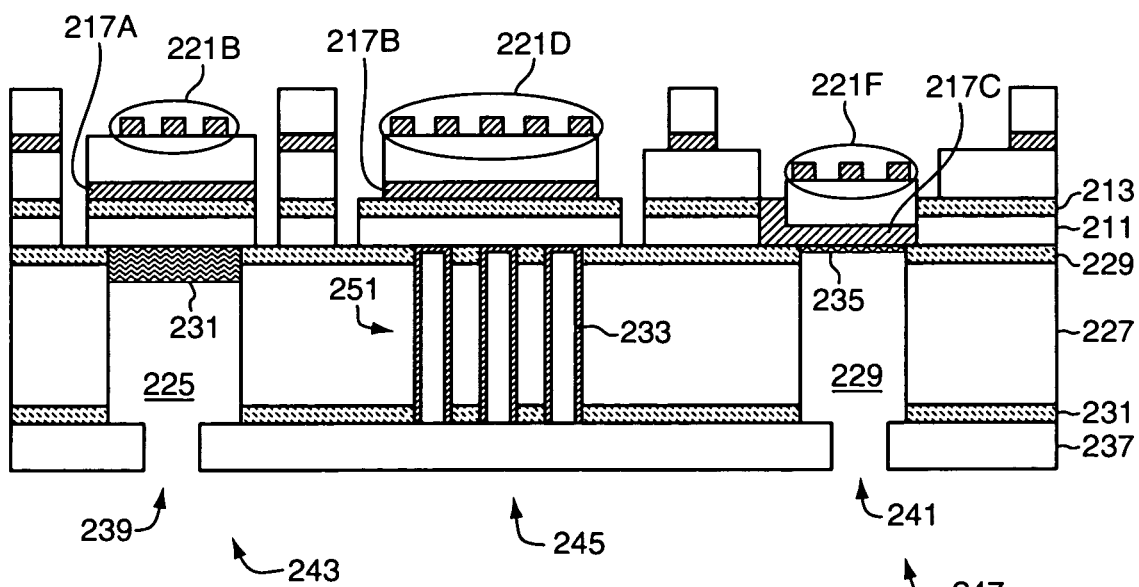

FIG. 15 shows a view after coupling a coverplate 237 having a sample inlet 239 and a sample outlet 241 to the backside of the substrate of FIG. 14, according to one or more embodiments of the invention. The approaches described above may optionally be used.

Now, the scope of the invention is not limited to the just the particular chemical analysis systems illustrated above. Many alternate chemical analysis systems are contemplated in which structures are omitted, rearranged, or added. Additionally, analogous chemical analysis systems may be formed on substrates other than standard silicon and SOI substrates.

V. Exemplary Chemical Analysis Systems Including Multiple FBAR Detectors

For simplicity, the chemical analysis systems above were described in terms of a single FBAR detector. However, in one or more embodiments of the invention, the chemical analysis systems described above, as well as other chemical analysis systems, may include multiple FBAR detectors. By way of example, the multiple FBAR detectors may be used to provide a reference FBAR detector and/or to provide FBAR detectors with different chemically functionalized surfaces.

In some implementations, the resonance frequency of an FBAR detector may be affected by environmental conditions, such as, for example, changes in temperature. Additionally, the resonance frequencies of FBAR detectors may sometimes vary within a wafer and/or from wafer to wafer due, at least in part, to unintended variation FBAR detector structure, such as, for example, film thickness, which may potentially arise from heterogeneous process conditions during device fabrication.

Figure 16:
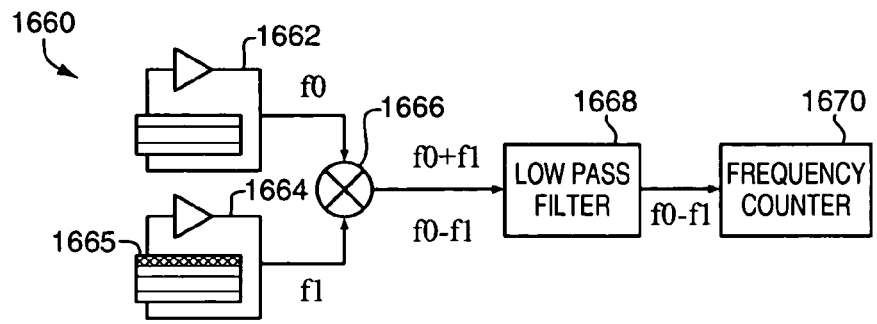
FIG. 16 shows a chemical analysis system including a reference FBAR detector, according to one or more embodiments of the invention.

FIG. 16 shows a chemical analysis system 1660 including an optional reference or control FBAR detector 1662 without a chemically functionalized electrode surface, an FBAR detector 1664 with a chemically functionalized electrode surface 1665, and circuitry to utilize the resonance frequencies of the FBAR detectors, according to one or more embodiments of the invention.

In one or more embodiments of the invention, the reference and chemically functionalized FBAR detectors may be fabricated proximate to one another within the chemical analysis system. As used herein, FBAR detectors are proximate to one another when they are within not more than 2 centimeters, such as, for example, within not more than 1 centimeter, or within 0.5 centimeters. The proximate FBAR detectors may tend to have about the same temperature and about the same structure due to similar process conditions during fabrication.

The reference FBAR detector may have a reference resonance frequency (f0), and the chemically functionalized FBAR detector may have a resonance frequency (f1). The frequency f1 may depend upon the attachment of a chemical species to the chemically functionalized surface. After optional amplification, a first signal representing the reference resonance frequency (f0) and a second signal representing the resonance frequency (f1) may be provided to a mixer 1666.

The mixer may potentially generate two signals representing the sum of the frequencies (f0+f1) and the difference of the frequencies (f0−f1), although these particular signals are not required. The sum and difference of the frequencies may be provided to a low pass filter 1668. The low pass filter may filter out the sum and provide the difference to a frequency counter 1670.

The differencing of the frequencies may help to reduce at least some of the affect on the resonance frequencies due to changes in environmental conditions (for example temperature) and/or due to variation in device structure. The affect of these factors may be similar on both resonance frequencies and may be substantially removed during the differencing process. This may potentially help to improve the accuracy and/or precision of the chemical analysis.

VI. First Exemplary Arrangement of FBAR Detectors

In some cases, different types of chemical species may potentially attach similarly to the same chemically functionalized surface. For example, a gas may not have a one-to-one correlation with a functionalized coating and the coating may not allow unique identification of the gas. However, it is generally much less likely that the different types of chemical species will attach similarly to all of a variety of different chemically functionalized surfaces. In one or more embodiments of the invention, a chemical analysis system may include multiple FBAR detectors with differently chemically functionalized electrode surfaces in order to help distinguish one type of chemical species from other types. The multiple FBAR detectors may help to provide a relatively more unique signature for a particular chemical species than a single FBAR detector with a single functionalized surface.

Figure 17:
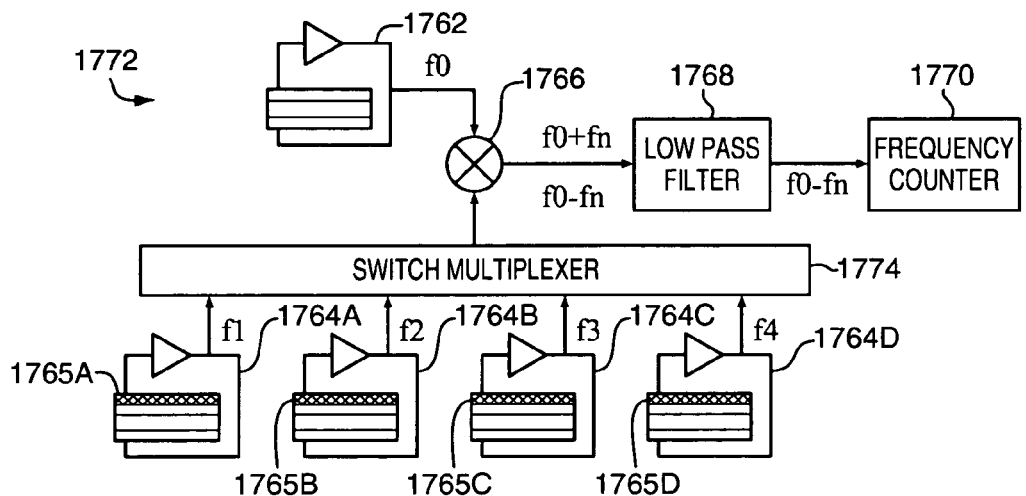
FIG. 17 shows a chemical analysis system having an arrangement of FBAR detectors that allows sequential collection of signals, according to one or more embodiments of the invention.
Figure 18:
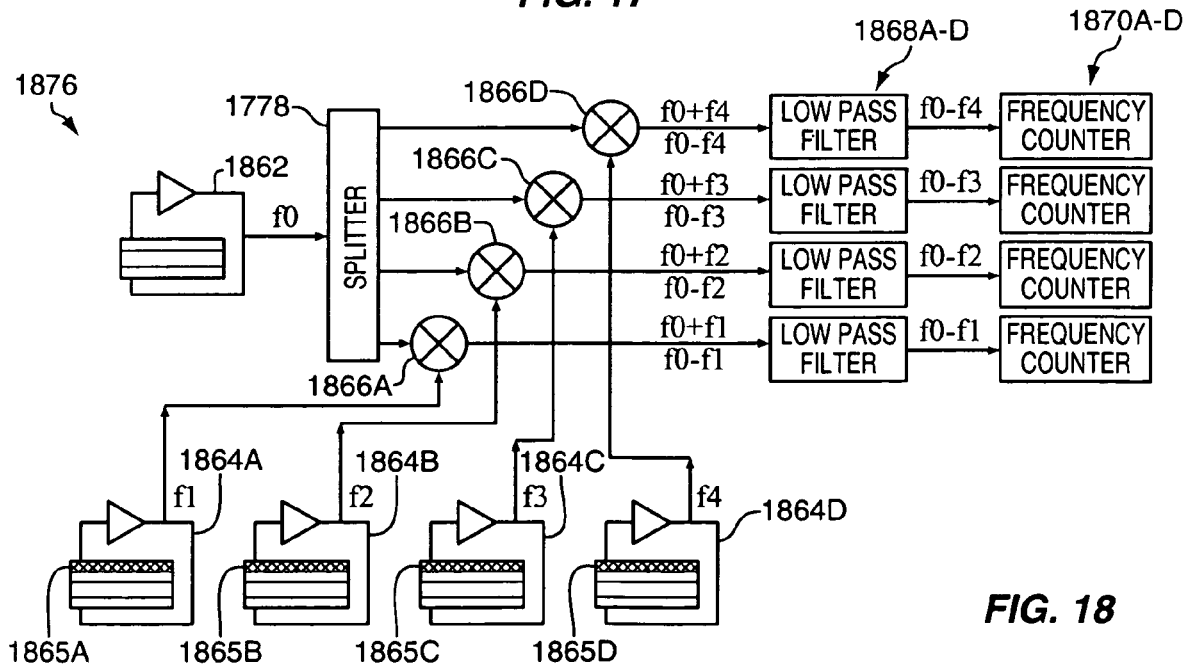
FIG. 18 shows a chemical analysis system having an arrangement of FBAR detectors that allows simultaneous collection of signals, according to one or more embodiments of the invention.

FIGS. 17-18 show chemical analysis systems with different exemplary arrangements of FBAR detectors having differently chemically functionalized electrode surfaces.

FIG. 17 shows a chemical analysis system 1772 having a first arrangement of FBAR detectors having differently chemically functionalized electrode surfaces, which allows sequential collection of signals from the FBAR detectors, according to one or more embodiments of the invention. The system includes an optional reference FBAR detector 1762, four chemically functionalized FBAR detectors 1764A-D that each have one of four corresponding different chemically functionalized electrode surfaces 1765A-D, a switch multiplexer 1774, a mixer 1766, a low pass filter 1768, and a frequency counter 1770.

The four differently chemically functionalized FBAR detectors are each coupled with the switch multiplexer. Each of the chemically functionalized FBAR detectors may provide a signal representing a resonance frequency to the switch multiplexer. In particular, a first FBAR detector 1764A may provide a signal representing a first resonance frequency (f1) to the switch multiplexer, a second FBAR detector 1764B may provide a signal representing a second resonance frequency (f2) to the switch multiplexer, and so on. A given type of chemical species may tend to attach at least somewhat differently to the four differently chemically functionalized electrodes than other types of chemical species. This generally tends to become even more true when more than four differently chemically functionalized electrodes are included, such as, for example, ten, twenty, or more.

The switch multiplexer is coupled with the mixer. The switch multiplexer may gather or otherwise collect the signals from the chemically functionalized FBAR detectors. In one or more embodiments, the switch multiplexer may collect the signals sequentially and in any desired order. In one or more embodiments of the invention, the switch multiplexer may optionally include logic to collect signals from a pertinent subset of the chemically functionalized FBAR detectors. The subset may be selected, for example, based on information about the particular chemical analysis performed, a particular chemical species of interest, or the like.

The switch multiplexer may provide the signals to the mixer. In one or more embodiments, the switch multiplexer may provide the signals sequentially. The mixer may optionally sequentially compare the resonance frequencies in turn with the reference resonance frequency that is provided to the mixer from the reference FBAR detector. For example, as shown in the illustrated embodiment, the mixer may determine a sum of the frequencies (f0+fn) and a difference of the frequencies (f0−fn), where fn may represent any one of the resonance frequencies f1, f2, f3, or f4. Each sum and difference may optionally be sequentially provided to the low pass filter, and then each difference may optionally be sequentially provided to the frequency counter, as previously described.

The resulting resonance frequency difference data collected through the frequency counter for the differently chemically functionalized FBAR detectors may be combined in order to generate a fingerprint or signature. A simple example of a fingerprint includes a list of frequency differences corresponding to the differently chemically functionalized FBAR detectors. The fingerprint may tend to be relatively more unique to the chemical species than data collected for any single chemically functionalized FBAR detector. At least to a point, a larger and more diverse set of differently chemically functionalized FBAR detectors may tend to provide a relatively more unique fingerprint that is better suited for chemical analysis.

The resulting fingerprint may be used for a variety of different purposes. In one or more embodiments of the invention, the fingerprint or signature may optionally be used for chemical analysis, such as, for example, chemical detection and/or identification. A method, according to one or more embodiments of the invention, may include comparing a determined fingerprint to one or more predetermined fingerprints, for example in a library, that each correspond to a different one or more known chemical species. In one or more embodiments of the invention, the method may further optionally include making an inference about detection and/or identification based on the comparison, although this is not required. For example, if the fingerprints match within a prescribed tolerance or uncertainty, then it may be inferred that the unknown chemical species was detected, or the identity of the unknown chemical species may be inferred to be the same as the known chemical species.

As another option, in one or more embodiments of the invention, the fingerprint or signature may be stored in a machine-accessible and/or machine-readable medium. In one aspect, fingerprints or signatures may be stored for different chemical species in order to generate a library that may be used in the future. The scope of the invention is not limited to detecting or identifying chemical species, additionally, even if detection or identification is desired, chromatography, and other information may be used to supplant the information from the FBAR detectors in order to improve the capability for detection and/or identification.

VII. Second Exemplary Arrangement of FBAR Detectors

FIG. 18 shows a chemical analysis system 1876 having an arrangement of FBAR detectors having differently chemically functionalized electrode surfaces that allows simultaneous collection of signals from the FBAR detectors, according to one or more embodiments of the invention. The system includes an optional reference FBAR detector 1862, a splitter 1778, four chemically functionalized FBAR detectors 1864A-D that each have one of four corresponding different chemically functionalized electrode surfaces 1865A-D, four mixers 1866A-D, four low pass filters 1868A-D, and four frequency counters 1870A-D.

As shown, the reference FBAR detector may be coupled with the splitter. The splitter may split the signal representing the reference resonance frequency into four corresponding signals. The splitter is coupled with each of the four mixers and may provide each of the four signals representing the reference resonance frequency to one of the four mixers. In one or more embodiments, the signals may be provided concurrently.

The four chemically functionalized FBAR detectors are each coupled with one of the four mixers. For example, a first FBAR detector 1864A is coupled with a first mixer 1866A, a second FBAR detector 1864B is coupled with a second mixer 1866B, and so on. The four differently chemically functionalized FBAR detectors may each provide a signal representing a corresponding resonance frequency to one of the four mixers. In one or more embodiments, the signals may be provided concurrently.

The four mixers may each compare the signals, such as, for example, as described above. The four mixers are each coupled with one of the four low pass filters and may provide comparison information to the filters.

The four low pass filters may filter the comparison information, such as, for example, as described above. The four low pass filters are each coupled with one of the four frequency counters and may provide the filtered information to the frequency counters.

Concurrent collection of signals may offer a potential advantage of accumulating or strengthening a potentially weak signal over time. This may potentially help to improve chemical analysis.

Now, the scope of the invention is not limited to just the above-described arrangements of FBAR detectors. Other arrangements may include either fewer or more than four chemically functionalized FBAR detectors. By way of example, two, five, ten, twenty, or more chemically functionalized FBAR detectors may optionally be included. Still other arrangements may lack the reference FBAR detector. Yet other arrangements may include some FBAR detectors in sequential arrangement and others in concurrent arrangement, etc.

By now it should be appreciate that many different types of samples and chemical species may be analyzed by the chemical analysis systems disclosed herein. In one or more embodiments of the invention, the sample may include a gas, although the scope of the invention is not limited in this respect. For example, the sample may include air, an ambient gas, a carrier gas, or another gas. The sample may at least potentially include one or more chemical species of interest. Suitable chemical species of interest include, but are not limited to, hazardous chemicals and biological molecules. Examples of suitable hazardous chemicals include, but are not limited to, warefare agents, explosives, pollutants, radon, and carbon dioxide, to name just a few examples. Examples of suitable biological molecules include, but are not limited to, proteins, nucleic acid derivatives (for example nucleic acids, nucleic acid fragments, nucleotides, nucleosides (e.g. adenosine, cytidine, guanosine, thymidine, uridine), bases (e.g. adenine, cytosine, guanine, thymine, uracil), purine, pyrimidine, biological sugars, and the like. Other suitable chemical species of interest include, but are not limited to, water, ammonia, chloroform, and the like. These are just examples of the types of samples and chemical species that may be analyzed.

VIII. Systems Including Chemical Analysis Systems

Figure 19:
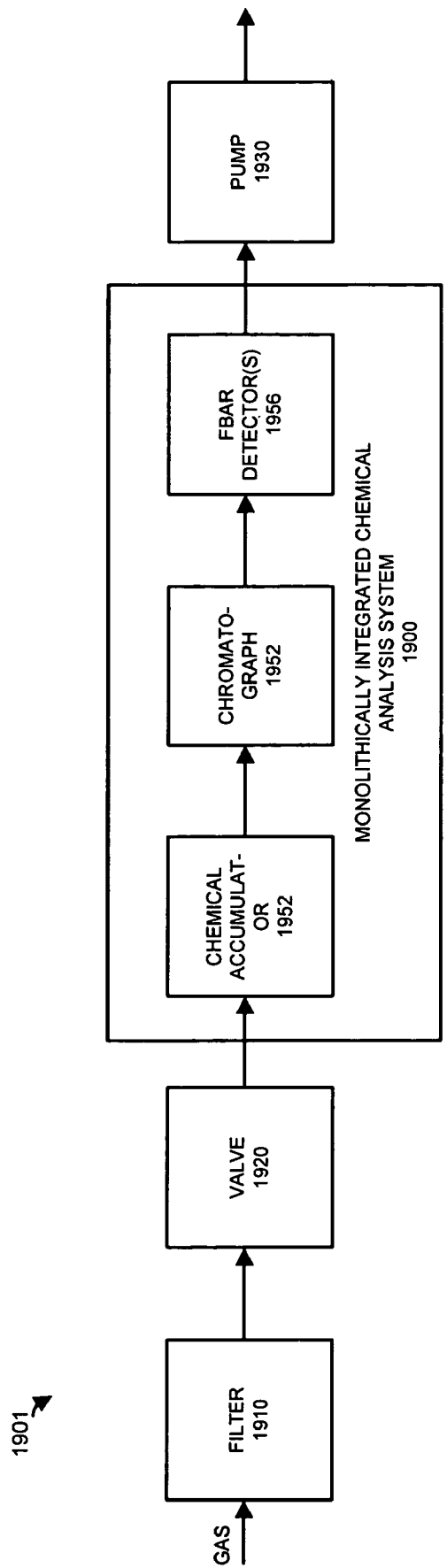
FIG. 19 shows a chemical analysis system in which a monolithically integrated chemical analysis system may be employed, according to one or more embodiments of the invention.

FIG. 19 shows a chemical analysis system 1901 in which a monolithically integrated chemical analysis system 1900 may be employed, according to one or more embodiments of the invention. The chemical analysis system 1901 includes an optional filter 1910, a valve 1920 having an inlet that is coupled with an outlet of the filter, the monolithically integrated chemical analysis system having an inlet that is coupled with an outlet of the valve, and a pump having an inlet that is coupled with an outlet of the monolithically integrated chemical analysis system. The scope of the invention is not limited to this particular connection of the monolithically integrated chemical analysis system 1900 with the other components. Other arrangements of valves (or other fluid flow regulation devices), and pumps (or fans or other devices to cause flow) are also contemplated. The monolithically integrated chemical analysis system includes an optional chemical accumulator 1952, a chromatograph 1954, and one or more FBAR detectors 1956, which may each have attributes as described elsewhere herein.

A representative method of use, according to one or more embodiments of the invention, may include opening the valve, activating the pump in order to pump gas through the filter, through the opened valve, and into the chemical accumulator. The gas introduced into the chemical accumulator may potentially include one or more chemical species that may be accumulated in the chemical accumulator. After a sufficient amount of accumulation, the valve may be closed, a heater may heat the chemical accumulation material to release the accumulated chemical species, and the chromatograph and FBAR detector may process the species as described above. The gas including any analyzed chemical species may be discharged from the pump, such as, for example, to atmosphere or another suitable destination.

Figure 20:
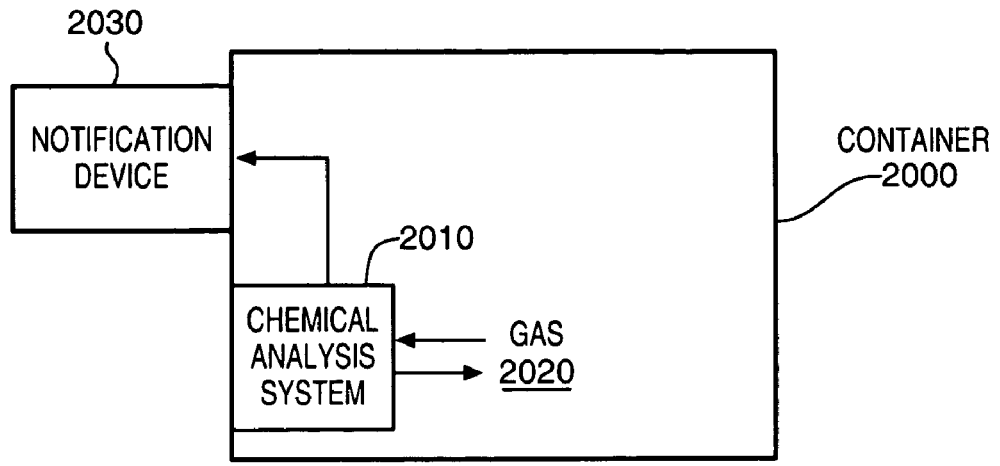
FIG. 20 shows a container having a chemical analysis system and a gas sealed or otherwise included therein, according to one or more embodiments of the invention.

FIG. 20 shows a container 2000 having a chemical analysis system 2010 and a gas 2020 sealed or otherwise included therein, according to one or more embodiments of the invention. Suitable containers include, but are not limited to, pressurized gas cylinders, fire extinguishers, commercial packages, pill bottles, and hazardous materials containers.

In one or more embodiments of the invention, the chemical analysis system may be used to detect a change in composition and/or pressure of the gas in the container based at least in part on a detected change in resonance frequency. For example, the chemical analysis system may detect entry of a foreign or ambient chemical species, such as, for example, air, oxygen, or nitrogen, into the container. As another example, the chemical analysis system may detect a reduction in concentration and/or pressure of a native chemical species in the container. Such detection may be used, for example, to detect and infer damage to the container, tampering with the container, and the like. The chemical analysis system may include one or more FBAR detectors and need not include either a chemical accumulator or a chromatograph, as these components are not required in this application.

As shown, in one or more embodiments of the invention, an optional notification device 2030 may be included outside the chamber and coupled with the chemical analysis system to provide a notification signal based on the chemical analysis, such as, for example, if a great enough change in resonance frequency is detected. One type of suitable notification device includes a speaker or other audible notification device. Another type of suitable notification device includes a light or other visual notification devices. Still another type of suitable notification device is includes both an audible and visual notification device. Yet another type of suitable notification device includes a wireless transmitter or transceiver to wirelessly transmit and/or receive information, such as, for example, to transmit chemical analysis information.

Figure 21:
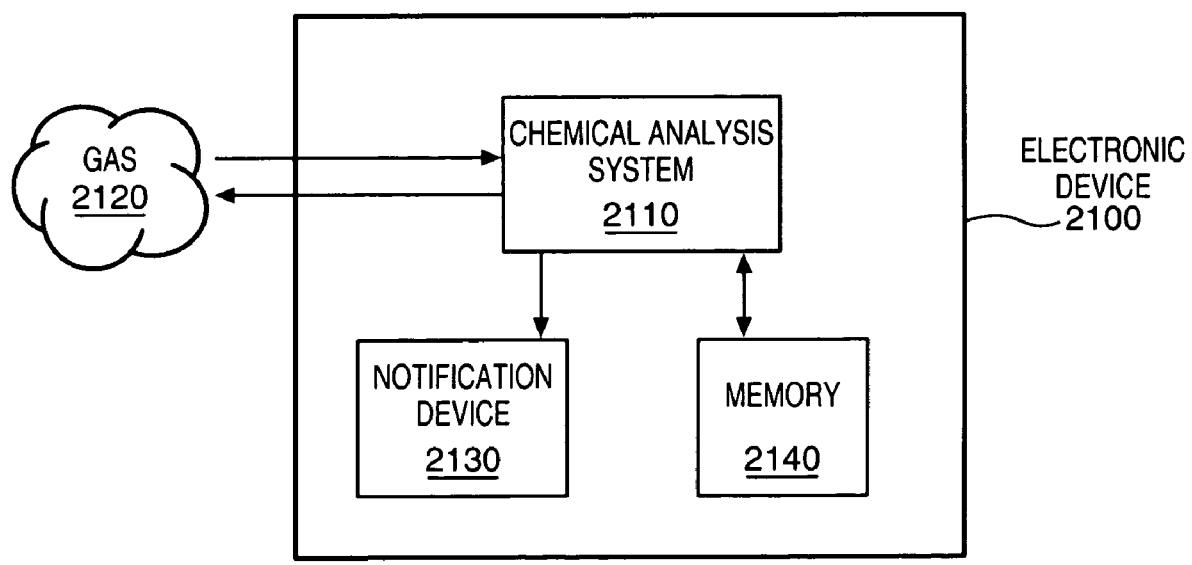
FIG. 21 shows an electronic device including a chemical analysis system, according to one or more embodiments of the invention.

FIG. 21 shows an electronic device 2100 including a chemical analysis system 2110, according to one or more embodiments of the invention. In one or more embodiments of the invention, the electronic device may include a mobile and wireless electronic device. Suitable mobile and wireless electronic devices include, but are not limited to, laptop computers, personal digital assistants, cellular phones, walkie-talkies, pagers, wireless communication devices, vehicles with wireless capability and potentially geographic positioning capability. Various other electronic devices are also suitable, such as, for example, desktop computers and watches, whether or not they are wireless or mobile.

In one or more embodiments of the invention, the chemical analysis system may be used to detect a chemical species in an ambient gas 2120. The electronic device may optionally have a notification device 2130 to notify the user based on the chemical analysis. Suitable notification devices include, but are not limited to, the notification devices mentioned above. In one aspect, alerts or other chemical analysis results may be displayed on a screen, provided by a speaker, or the like. In an aspect, the chemical analysis system may couple with a wireless transmitter and may transmit analysis information, such as, for example, an alert signal.

The electronic device may also have a memory 2140. The memory may provide a machine-accessible and/or readable medium that may be used to store chemical analysis instructions, such as, for example, fingerprint comparison instructions, data useful for performing chemical analysis, such as, for example, predetermined fingerprints, and chemical analysis result data. Certain electronic devices may have static-RAM (SRAM), while other electronic devices may have dynamic-RAM (DRAM), while still other electronic devices may have a Flash memory. Other electronic devices may have other types of memory known in the arts.

In one or more embodiments of the invention, the electronic device having the chemical analysis system may be included in a chemical sensor network. The network may include a plurality of potentially different types of electronic devices that may report chemical analysis results to a data collection center. Without limitation on the scope of the present invention, the chemical analysis results may be analyzed to determine the location and/or the spread of hazardous chemicals, such as, for example, pollutants, explosives, warefare agents, biological weapons, and materials of mass destruction, or other chemical species of interest.

According to one or more embodiments of the invention, chemical analysis systems and/or electronic devices having chemical analysis systems may be included in a manufacturing facility, such as, for example, a semiconductor fabrication facility. Without limitation, the chemical analysis systems may be used to detect chemical species in the air and/or perform other environmental monitoring or other functions known to be potentially useful in a semiconductor fabrication facility IX. Other Matters In the description above, for the purposes of explanation, numerous specific details have been set forth in order to provide a thorough understanding of the embodiments of the invention. It will be apparent however, to one skilled in the art, that one or more other embodiments may be practiced without some of these specific details. In other instances, well-known circuits, structures, and devices, have been shown in block diagram form or without detail in order to avoid obscuring the understanding of the description.

In addition, it is to be realized that the scope of the invention is to encompass variations in size, materials, shape, form, function and manner of operation, assembly and use, of the embodiments and components of the invention as are deemed readily apparent to one of ordinary skill in the art. All equivalents to those illustrated in the drawings and described in the specification are encompassed by the present invention. For simplicity and/or to facilitate illustration, certain components illustrated in the figures have not been drawn to scale and may instead have been exaggerated.

In the description and claims, the terms "coupled" and "connected," along with their derivatives, may be used. "Connected" may be used to indicate that two or more elements are in direct physical and/or electrical contact with each other. "Coupled" may also mean that two or more elements are in direct physical and/or electrical contact. However, "coupled" may also mean that two or more elements are not in direct physical and/or electrical contact with each other, but yet may still co-operate or interact with each other, such as, for example, through one or more other components or materials.

Various operations and methods have been described. Operations may optionally be added to and/or removed from the methods. Also, operations may optionally be performed in a different order. Many modifications and adaptations to the methods are contemplated. The particular embodiments described are not provided to limit the invention but for purposes of illustration. The scope of the invention is not to be determined by the specific examples provided above but only by the claims below.

One or more embodiments of the invention may be provided as a program product or other article of manufacture that may include a machine-accessible and/or readable medium having stored thereon one or more instructions and/or data structures, such as, for example, chemical analysis instructions and/or predetermined fingerprints and/or fingerprint comparison instructions. The medium may provide instructions, which, if executed by a machine, may result in and/or cause the machine to perform one or more of the operations or methods disclosed herein. Suitable machines include, but are not limited to, the electronic devices disclosed above and various other devices with one or more processors. The medium may include a mechanism that provides or stores information in a form that is accessible by the machine. For example, the medium may optionally include recordable and/or non-recordable mediums, such as, for example, floppy diskette, optical storage medium, optical disk, CD-ROM, magnetic disk, magneto-optical disk, read only memory (ROM), programmable ROM (PROM), erasable-and-programming ROM (EPROM), electrically-erasable-and-programmable ROM (EEPROM), random access memory (RAM), static-RAM (SRAM), dynamic-RAM (DRAM), Flash memory, and combinations thereof.

For clarity, in the claims, any element that does not explicitly state "means for" performing a specified function, or "step for" performing a specified function, is not to be interpreted as a "means" or "step" clause as specified in 35 U.S.C. Section 112, Paragraph 6. In particular, any potential use of "step of" in the claims herein is not intended to invoke the provisions of 35 U.S.C. Section 112, Paragraph 6.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

Accordingly, while the invention has been thoroughly described in terms of several embodiments, those skilled in the art will recognize that the invention is not limited to the particular embodiments described, but may be practiced with modification and alteration within the spirit and scope of the appended claims. The description is thus to be regarded as illustrative instead of limiting.

What is claimed is:

1. An apparatus comprising:
   a monolithic substrate;
   a chromatograph including a channel that is defined at least partially in the monolithic substrate, the channel having an inlet to receive a sample and an outlet, and the chromatograph including a chromatography material in the channel;
   a patterned layer disposed over the monolithic substrate;
   a bulk acoustic resonator having a first electrode, and a second electrode that has a chemically functionalized surface that is included in a chamber, wherein the chamber is defined at least partially in the monolithic substrate and is coupled with the outlet of the chromatograph, and wherein the first electrode is part of the patterned layer;
   a chemical accumulator coupled with the inlet of the channel, the chemical accumulator including a chamber that is defined at least partially in the monolithic substrate and that has a chemical accumulation material therein;
   a first heater which is part of the patterned layer coupled with the chemical accumulator to heat the chemical accumulation material; and
   a second heater which is part of the patterned layer coupled with the chromatograph to heat the chromatography material.

2. The apparatus of claim 1, wherein the bulk acoustic resonator comprises a film bulk acoustic resonator.

3. The apparatus of claim 1, wherein the first electrode comprises one or more metal traces comprising a resistive heating element that is operable to heat the second electrode.

4. The apparatus of claim 1, wherein said monolithic substrate is a piece of single crystal silicon.

5. An apparatus comprising:
   a substrate comprising a piece of single crystal silicon;
   a chromatograph including a channel that is defined at least partially in the piece of single crystal silicon, the channel having an inlet to receive a sample, the channel having a chromatography material therein to affect progression of chemical species of the sample through the channel, and the channel having an outlet;
   a patterned layer disposed over the piece of single crystal silicon;
   a first heater comprising one or more metal traces which is part of the patterned layer and which is positioned adjacent to the chromatograph to heat the material in the channel; and
   a film bulk acoustic resonator (FBAR) detector, the FBAR detector including a first electrode which is part of the patterned layer, a second electrode having a coated surface, and a piezoelectric material disposed between the first and the second electrodes, the FBAR detector further including a chamber that is defined at least partially in the piece of single crystal silicon, the chamber having an inlet that is coupled with the outlet of the chromatograph to receive the chemical species, wherein the coated surface of the second electrode is exposed to the chamber of the FBAR detector.

6. The apparatus of claim 5, further comprising: a chemical accumulator including a second chamber that is defined at least partially in the piece of single crystal silicon, the second chamber having an inlet to receive the sample, the chamber having a sorbent therein to sorb the sample, and the chamber having an outlet that is coupled with the inlet of the channel; and a second heater comprising one or more metal traces positioned adjacent to the chemical accumulator to heat the sorbent.

7. The apparatus of claim 5, wherein the first electrode comprises one or more metal traces comprising a resistive heating element that is operable to heat the second electrode.

8. The apparatus of claim 5, wherein the outlet of the channel and the inlet of the chamber of the FBAR detector are coupled via a microchannel.

9. The apparatus of claim 5, wherein the piece of the single crystal silicon comprises bulk silicon of a silicon-on-insulator substrate.

10. An apparatus comprising:
    a chemical analysis system including:
    a monolithic substrate;
    a chromatograph including a channel that is defined at least partially in the monolithic substrate, the channel having an inlet to receive a sample and an outlet, and the chromatograph including a chromatography material in the channel;
    a patterned layer disposed over the monolithic substrate;
    a bulk acoustic resonator having a first electrode, and a second electrode that has a chemically functionalized surface that is included in a chamber, wherein the chamber is defined at least partially in the monolithic substrate and is coupled with the outlet of the channel; and wherein the first electrode comprises a metal trace that is part of the patterned layer, wherein the metal trace comprises a resistive heating element that is operable to heat the second electrode.

11. The apparatus of claim 10, wherein the bulk acoustic resonator comprises a film bulk acoustic resonator.

12. The apparatus of claim 10, wherein said monolithic substrate is a piece of single crystal silicon.

13. The apparatus of claim 10, further comprising a wireless transmitter coupled with the chemical analysis system.

14. The apparatus of claim 10, implemented in a laptop computer.

15. The apparatus of claim 10, implemented in a cellular phone.

16. The apparatus of claim 10, further comprising a heater coupled with the chromatograph to heat the chromatograph, and wherein the heater that is coupled with the chromatograph and the first electrode are different portions of the patterned layer.

17. The apparatus of claim 10, wherein the monolithic substrate comprises a silicon-on-insulator substrate.

18. The apparatus of claim 10, further comprising a Flash memory coupled with the chemical analysis system to store data.

* * * * *